(12) United States Patent
Gad et al.

(10) Patent No.: US 11,517,408 B2
(45) Date of Patent: Dec. 6, 2022

(54) METHOD FOR TREATING DENTURE STOMATITIS USING DENTURE BASE MATERIAL CONTAINING NANODIAMONDS

(71) Applicant: Imam Abdulrahman Bin Faisal University, Dammam (SA)

(72) Inventors: Mohammed Moustafa Ahmed Gad, Dammam (SA); Shaimaa Mohamed Said Fouda, Dammam (SA); Fahad A. Al-Harbi, Dammam (SA); Ahmad M. Al-Thobity, Dammam (SA); Passent Safwat Aly Ellakany, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 127 days.

(21) Appl. No.: 17/078,756

(22) Filed: Oct. 23, 2020

(65) Prior Publication Data

US 2021/0121272 A1 Apr. 29, 2021

Related U.S. Application Data

(60) Provisional application No. 62/925,014, filed on Oct. 23, 2019.

(51) Int. Cl.
*A61C 13/087* (2006.01)
*A61K 6/887* (2020.01)

(52) U.S. Cl.
CPC ............ *A61C 13/087* (2013.01); *A61K 6/887* (2020.01)

(58) Field of Classification Search
CPC ..... A61C 13/01; A61C 13/10; A61C 13/1003; A61C 13/00; A61C 13/0025; A61C 13/08; A61C 13/087; A61K 6/80–898
See application file for complete search history.

(56) References Cited

U.S. PATENT DOCUMENTS

| 9,737,632 B2 | 8/2017 | Johnson et al. |
| 2018/0296306 A1 * | 10/2018 | Kohgo ..................... A61K 6/30 |

FOREIGN PATENT DOCUMENTS

| CN | 101518499 B | | 3/2011 | |
| CN | 107440912 A | | 12/2017 | |
| CN | 105120960 B | | 6/2018 | |
| DE | 102008028306 A1 | * | 12/2009 | ........ A61C 13/0003 |
| EP | 1 913 927 A1 | | 4/2008 | |
| KR | 20180089219 A | * | 8/2018 | |
| KR | 10-1916171 B1 | | 11/2018 | |
| WO | WO-2005097045 A1 | * | 10/2005 | ............. A61K 33/44 |
| WO | WO-2008015453 A1 | * | 2/2008 | ............. A01N 59/16 |
| WO | WO-2018119026 A1 | * | 6/2018 | ............... A61C 7/00 |

OTHER PUBLICATIONS https://www.medicalnewstoday.com/articles/322722 (Year: 2018).*

(Continued)

*Primary Examiner* — Edward Moran
*Assistant Examiner* — Luis M Ruiz Martin
(74) *Attorney, Agent, or Firm* — Oblon, McClelland, Maier & Neustadt, L.L.P.

(57) ABSTRACT

A curable composite material containing nanodiamonds, denture bases and other dental prosthetics made from the composite material and methods for treating dental stomatitis using these prosthetics.

11 Claims, 4 Drawing Sheets

(56) References Cited

OTHER PUBLICATIONS https://www.sciencedirect.com/topics/medicine-and-dentistry/polymethyl-methacrylate (Year: 2017).*
https://my.clevelandclinic.org/health/diseases/21702-denture-stomatitis#:~:text=Denture%20stomatitis%20is%20one%20of,those%20who%20wear%20partial%20dentures (Year: 2021).*
https://www.prosthodontics.org/about-acp/position-statement-the-frequency-of-denture-replacement/ (Year: 2018).*
V. Tamara Perchyonok, et al., "Bio-Active Nano-Diamond Designer Materials and Dentures: From Design to Application", Dentistry, vol. 5, Issue 11, 2015, pp. 1-6.
Popi Protopapa, et al., "Reinforcement of a PMMA resin for fixed interim prostheses with nanodiamonds", Dental Materials Journal, vol. 30, No. 2, 2011, pp. 222-231.
N. Gopi Chander, "Polymethyl metha acrylate denture base: An overview", The Journal of Indian Prosthodontic Society, 2018, pp. 87-88.
Vadym N. Mochalin, et al., "Nanodiamond-polymer composites", Diamond & Related Materials, vol. 58, 2015, pp. 161-171.
Shaimaa M. Fouda, et al., "The effect of nanodiamonds on candida albicans adhesion and surface characteristics of PMMA denture base material—an in vitro study", Journal of Applied Oral Science, JAOS, vol. 27, 2019, pp. 1-10.

* cited by examiner

FIG. 2A
FIG. 2B
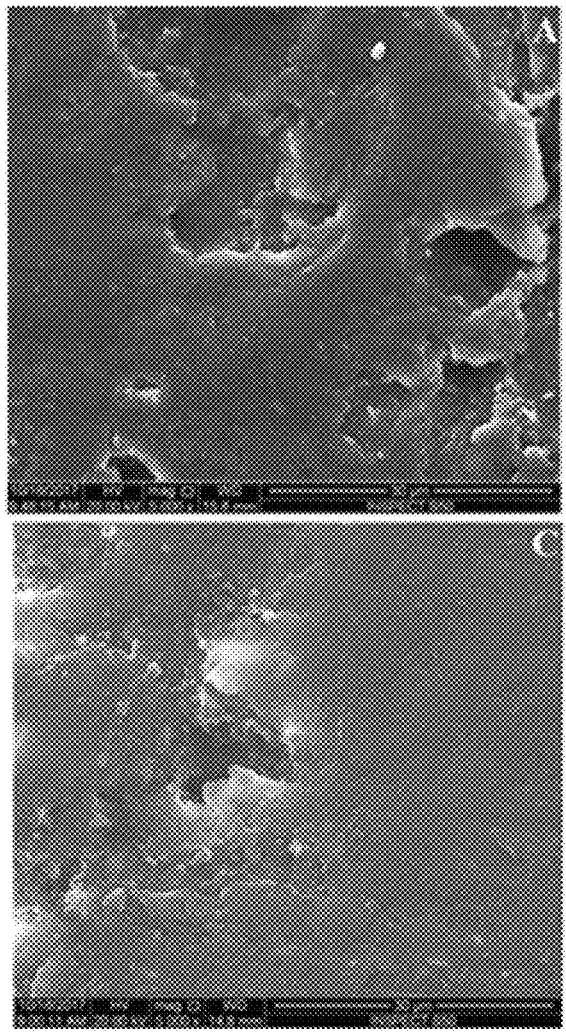
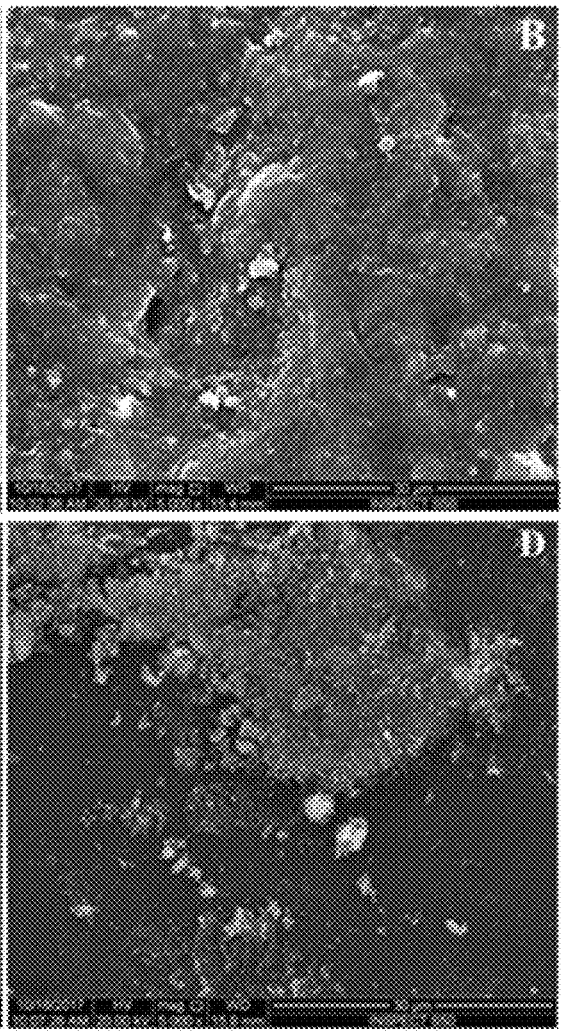
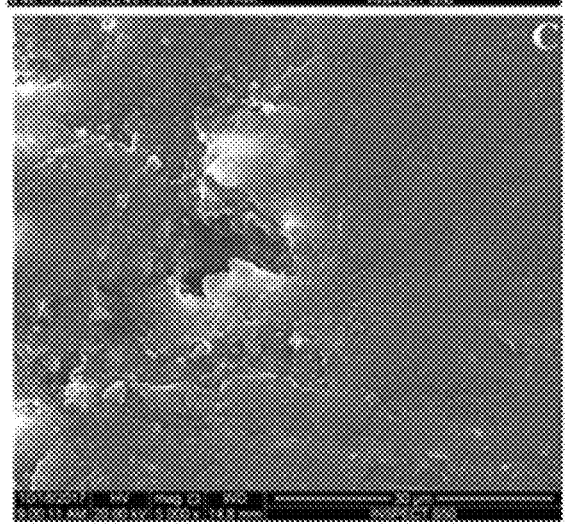
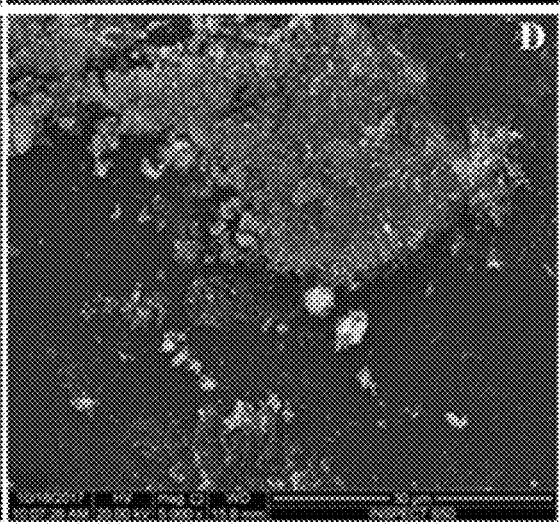
FIG. 2C
FIG. 2D

METHOD FOR TREATING DENTURE STOMATITIS USING DENTURE BASE MATERIAL CONTAINING NANODIAMONDS

CROSS-REFERENCE TO RELATED APPLICATIONS

This application is based on, and claims the benefit of priority to, provisional Application No. 62/925,014, filed Oct. 23, 2019, the entire contents of which are incorporated herein by reference.

BACKGROUND OF THE INVENTION

Field of the Invention

The invention pertains to the fields of dental and oral medicine, microbiology, and to the use of nanodiamonds to treat or prevent denture stomatitis associated with *Candida albicans* and other yeasts.

Description of Related Art

Edentulousness increases in old age and in such cases, a conventional complete denture is commonly the treatment of choice; Fouda S M, et al., *Missing teeth and prosthetic treatment in patients treated at College of Dentistry, University of Dammam*. Int J Dent. 2017. Denture bases are constructed from metal and/or acrylic resin. Acrylic resin, however, is more frequently used due to its ease of construction and repair, aesthetics and low cost, despite the material's drawbacks of high surface roughness and low strength; Nandal S, et al., *New era in denture base resins: A review*. Dental Journal of Advance Studies. 2013 December; 1(03):136-43.

Denture stomatitis (DS) affects more than 70% of patients wearing complete dentures; Gendreau L, et al., *Epidemiology and etiology of denture stomatitis*. J Prosthodont. 2011 June; 20(4):251-60. Many factors, such as poor oral hygiene; poor-fitting dentures; rough, porous denture surfaces and systemic diseases, are associated with DS, of which *Candida albicans* is considered the main causative pathogen. The hydrophobicity and surface roughness of denture bases affect the primary attachment and colonization of *Candida albicans*; Gendreau L, et al., id; Pereira T, et al., *In vitro Candida colonization on acrylic resins and denture liners: influence of surface free energy, roughness, saliva, and adhering bacteria*. Int J Prosthodont. 2007 May 1; 20(3).

Conventional ways to reduce the incidence of DS include mechanical cleansing, chemical disinfection, special coatings, and/or incorporating antimicrobial agents in the denture base material; Izumida F E, et al. *In vitro evaluation of adherence of Candida albicans, Candida glabrata, and Streptococcus mutans to an acrylic resin modified by experimental coatings*. Biofouling. 2014 May 28; 30(5):525-33; Ali A A, et al., *Effectiveness of coating acrylic resin dentures on preventing Candida adhesion*. J Prosthodont. 2013 August; 22(6):445-50; Nawasrah A, et al., *Antifungal effect of henna against Candida albicans adhered to acrylic resin as a possible method for prevention of denture stomatitis*. Int J Environ Res Public Health 2016 May 23; 13(5):520; Da Silva F C, et al. *Effectiveness of six different disinfectants on removing five microbial species and effects on the topographic characteristics of acrylic resin*. J Prosthodont. 2008 December; 17(8):627-33.

Conventional cleaning methods are usually effective at eliminating plaque accumulation from dentures, Da Silva, R C, et al., id. However, performing them may be challenging for elderly patients, particularly those with physical disabilities or in need of nursing care.

Oral antifungal agents are effective in the treatment of DS, but have toxic side effects and may lead to the development of resistant strains. In addition, DS recurrence commonly occurs with their use; Garcia-Cuesta C, et al., *Current treatment of oral candidiasis: A literature review*. J Clin Exp Dent. 2014; 6:576-582. The antimicrobial effect of chemical disinfectants is related to their proper use according to the preparation guidelines and immersion time; Al-Thobity A M et al., *Impact of Denture Cleansing Solution Immersion on Some Properties of Different Denture Base Materials: An In Vitro Study*. J Prosthodont. 2017; 1-7.

Many studies have investigated the effect of adding antimicrobial or antifungal agents to a denture base resin in an attempt to reduce microbial and/or fungal adhesion and thereby prevent DS; Sawada T, et al., *Self-cleaning effects of acrylic resin containing fluoridated apatite-coated titanium dioxide*. Gerodontology. 2014 March; 31(1): 68-75; Nam K Y, et al., *Antifungal and physical characteristics of modified denture base acrylic incorporated with silver nanoparticles*. Gerodontology. 2012; 29(2):e413-19; Li Z, et al., *Effect of a denture base acrylic resin containing silver nanoparticles on Candida albicans adhesion and biofilm formation*. Gerodontology. 2016 June; 33(2): 209-16. However, as explained above, the incorporation of antibacterial or antifungal agents can produce toxic side-effects, cause inflammation, disrupt the normal oral biota, or result in development of resistant microorganisms especially when used over an extended period of time, such over the lifetime of dentures.

Moreover, the use of these cleaning or disinfection procedures can adversely affect the physical properties of a denture base resin leading to increased surface roughness, color changes and reduced flexural strength; Al Thobity, A M, et al., id; Eg-Porwal A, et al., *Effect of denture cleansers on color stability, surface roughness, and hardness of different denture base resins*. J Indian Prosthodont Soc 2017; 17:61-67.

Surface roughness (Ra) and hydrophobicity are important properties of the denture base material that influence plaque and microbial adhesion and, subsequently, DS; Yamauchi M, et al. *In vitro adherence of microorganisms to denture base resin with different surface texture*. Dent Mater J. 1990 Jun. 25; 9(1):19-24; Radford D R, et al. *Adherence of Candida albicans to denture base materials with different surface finishes*. J Dent. 1998 Sep. 1; 26(7):577-83. A rough denture surface provides more area for microbial adhesion. In addition, it protects entrapped microorganisms from shearing forces during denture cleaning, making their removal difficult even with the use of antimicrobial agents; Pereira-Cenci T, et al. *Development of Candida-associated denture stomatitis: new insights*. J Appl Oral Sci 2008; 16(2):86-94; Waltimo T, et al. *Adherence of Candida species to newly polymerized and water-stored denture base polymers*. Int J Prosthodont. 2001; 14, 457-460.

Denture surfaces with high hydrophobicity have increased adhesion to *Candida albicans* due to the hydrophobic interaction between the bacteria and the denture base resin; Waltimo, T. et al., id. Recent attempts to enhance the antimicrobial, mechanical and physical properties of polymethylmethacrylate (PMMA) involving the addition of silver, platinum or titanium nanoparticles; has attracted attention because these microparticles enhance the mechanical and physical properties of the resin as well as its antimicrobial resistance. Al Harbi et al. *Effect of nanodiamond addition on flexural strength, impact strength, and surface roughness of PMMA denture base.* J Prosthodont. 2019; 28:417-425 reported improvement in the mechanical properties of ND-reinforced PMMA.

Several nanosized materials, such as silver, platinum, and titanium, have been added to PMMA, resulting in better resistance to bacterial and fungal colonization; Gad M M, et al., *A. PMMA denture base material enhancement: a review of fiber, filler, and nanofiller addition.* Int J Nanomedicine 2017; 12:3801; Wang X, et al., *Shape-dependent antibacterial activities of $Ag_2O$ polyhedral particles.* Langmuir. 2009 Oct. 9; 26(4):2774-8.

Work has been performed using nanodiamonds in the fields of medicine and dentistry, including guided tissue regeneration, polymer reinforcement, and antibacterial dental implant coatings; Szunerits S, et al. *Antibacterial applications of nanodiamonds.* Int J Environ Res Public Health 2016 Apr. 12; 13(4):413; Najeeb S, et.al. *Dental applications of nanodiamonds.* Sci Adv Mater. 2016 Nov. 1; 8(11): 2064-70; Lee DK, et.al. *Nanodiamond-gutta percha composite biomaterials for root canal therapy.* ACS nano. 2015 Oct. 15; 9(11):11490-501. NDs possess multiple reactive groups ($NH_2$, OH) that improve their interfacial bond with PMMA, and are thus considered a compatible filler material; Maitra U, et al., *Mechanical properties of nanodiamond-reinforced polymer-matrix composites.* Solid State Commun. 2009 Oct. 1; 149(39-40):1693-7; Mochalin V N, et al. *The properties and applications of nanodiamonds.* Nat. Nanotechnol 2012 JaAn; 7(1):11. Although studies have reported on the antimicrobial effect of NDs, none have investigated their effect against *Candida albicans* adhesion.

As explained above, denture stomatitis is a significant problem for people wearing dentures. *Candida albicans* plays a significant role in the morbidity of DS. Accordingly, the inventors sought to develop a way to reduce the severity of DS by identifying materials that prevent the adhesion of *Candida albicans* to dentures and other removable dental prostheses.

BRIEF SUMMARY OF THE INVENTION

As disclosed herein, the inventors have produced a dental composite material containing nanodiamonds that inhibits the attachment of yeasts such as *Candida albicans* to dentures and other dental prosthetics. Surprisingly, despite the high surface area of nanodiamond particles, the nanodiamonds increased the smoothness of the dental material while not substantially increasing its hydrophobicity as determined by scanning electron microscopy and by water contact angle.

The incorporation of nanodiamonds, particularly at low concentrations, reduces *Candida* adhesion and improves surface roughness.

Aspects of the invention include a method for preventing or treating dental stomatitis by providing a dental composite material resistant to attachment of the *Candida albicans* yeast which provides resistance to dental stomatitis.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings below.

FIG. 2. Representative SEM images of the tested specimens' surfaces. Unmodified specimens (FIG. 2A); 0.5% ND concentration (FIG. 2B); 1% ND concentration (FIG. 2C); 1.5% ND concentration (FIG. 2D).

DETAILED DESCRIPTION OF THE INVENTION

Figure 1A:
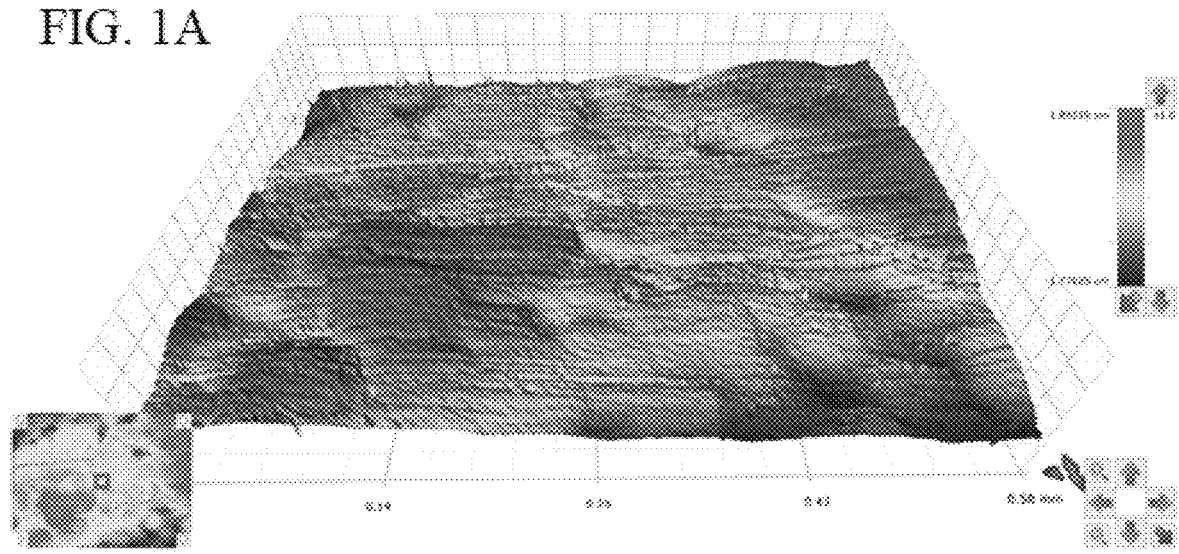
FIGS. 1A-1D. Representative surface images of: Unmodified specimens (FIG. 1A), 0.5% ND concentration (FIG. 1B); 1% ND concentration (FIG. 1C); 1.5% ND concentration (FIG. 1D).
Figure 1B:
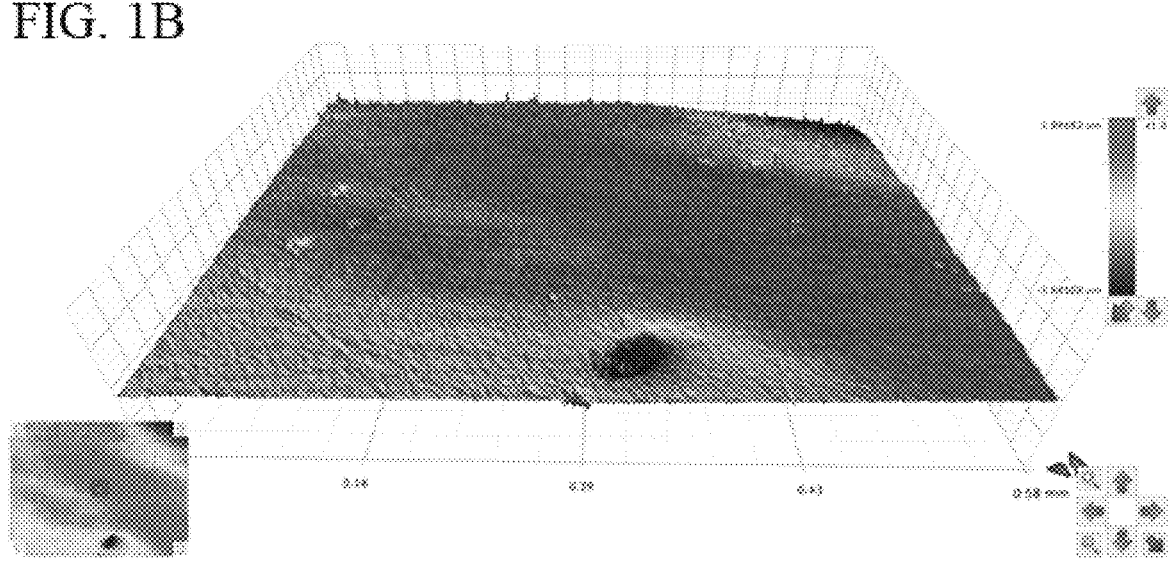
Figure 1C:
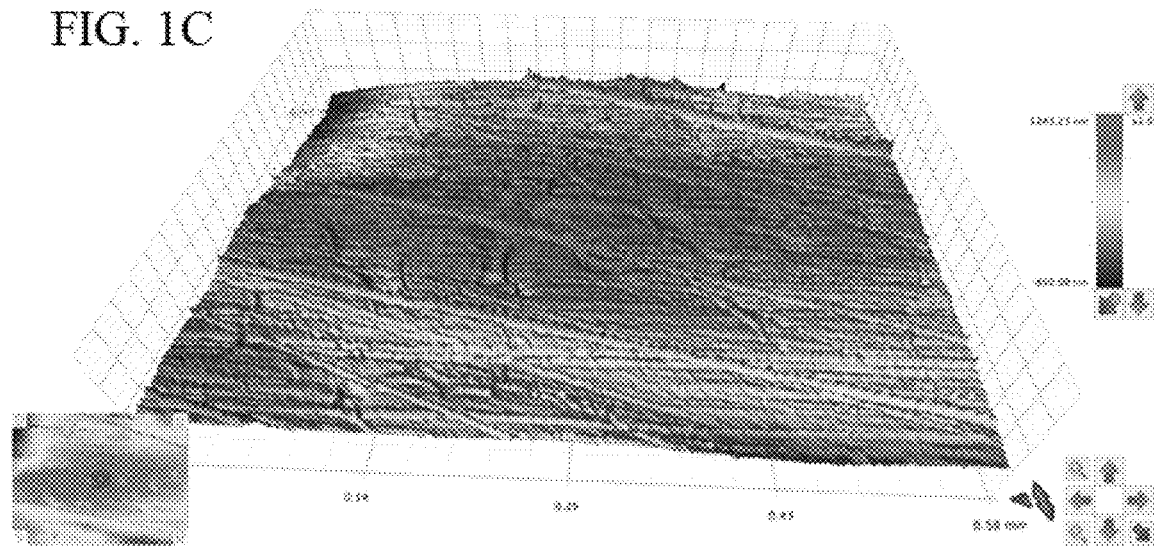
Figure 1D:
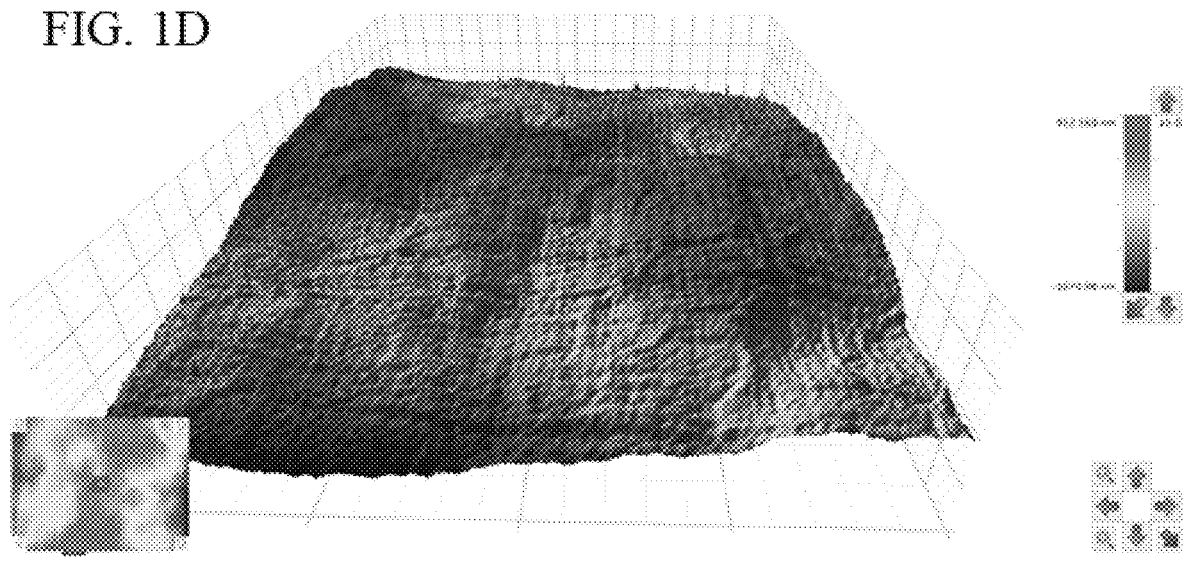

One embodiment of the invention is directed to a method for reducing the severity of denture stomatitis comprising providing a subject in need thereof a prosthetic comprising a composite material incorporating nanodiamonds. Typically, the subject will have been previously fitted with dentures to which yeasts such as *Candida albicans* attach and induce one or more symptoms of denture stomatitis or will be at risk of developing denture stomatitis, for example, an at-risk subject may have high blood sugar, eat a high carbohydrate diet, have diabetes, have cancer or leukemia, HIV/AIDS, be immunosuppressed, have xerostomia, be a smoker, or be on a drug such as an antibiotic, corticosteroid, or immunosuppressive drug, that can affect the natural microbial flora or impair or perturb the subject's immune system.

*Candida albicans* or other yeasts such as *C. tropicalis, C. glabrata, C. rugosa, C. parapsilosi, C. dubliniensis,* or *C. auris* may cause primary denture stomatitis as well as other secondary infections, such as to the mouth, throat and esophagus.

DS may be classified as type 1 (localized inflammation or pinpoint hyperemia), type 2 (diffuse erythema involving part or all of the mucosa in contact with the denture) or type 3 (exhibiting an inflammatory nodular/papillary hyperplasia which may be on the central hard palate or alveolar ridge).

Symptoms of secondary infections include thrush, white patches on the inner cheeks, tongue, roof of the mouth or throat, redness or soreness in the mouth, throat or esophagus, a cotton-like feeling in the mouth, loss of taste, pain while eating or swallowing or cracking or redness at the corners of the mouth. Thus, a subject with primary symptoms of DS or secondary symptoms of yeast infection may be selected for fitting with a denture or dental prosthetic containing nanodiamonds as disclosed herein. In a typical embodiment, a subject will have been fitted with dentures and have one or more symptoms of DS caused by attachment of *Candida albicans* to the denture.

A subject may be male or female, old or young, who has been fitted with or other dental prosthetics associated with stomatitis or a yeast infection, for example, a subject with dentures may be up to 25, 30, 35, 40, 45, 50, 55, 60, 65, 70, 75, 80, 85, 90, 95, 100 or >100 years old. A female subject may be pregnant or may be undergoing fertility treatments with drugs that reduce susceptibility to yeast infections.

The method disclosed herein may be used to treat a subject having xerostomia, periodontal disease, diabetes, or be infected with human immunodeficiency virus (HIV) or is immunosuppressed.

In the method disclosed herein, the composite material comprises a polymer suitable for use as a denture base, such as polymethylmethacrylate ("PMMA") and may be a heat-cured or light-cured polymethylmethacrylate ("PMMA"). In some embodiments the polymer is PMMA and has a molecular weight as measured by gel permeation chromatograph (GPC) of 50,000, 100,000, 200,000, 500,000, 1,000,000, 1,200,000, 1,500,000, 2,000,000, 2,100,000, 2,200,000, 2,500,000 to 3,000,000 or any intermediate value or subrange, for example, from 300,000 to 2,000,000.Poly(methyl methacrylate) used widely for prosthetic purposes, it is an amorphous, translucent, thermoset polymer with a chemical formula $(C_5O_2H_8)_x$ formed by the polymerization of MMA monomer. The molecular of PMMA affects polymer properties such as tensile strength, impact strength, fracture toughness and fatigue resistance. PMMA showed optimum mechanical properties with average molecular weight of $10^5$; see Huggett R, Bates J F, Packham D E. *The effect of the curing cycle upon the molecular weight and properties of denture base materials*. Dent Mater. 1987 June; 3(3):107-12 (incorporated by reference)

In the method disclosed herein, the composite material comprises nanodiamonds have an average diameter ranging from <10, 10, 20, 30, 40, 50, 60, 70, 80, 90, 100 or >100 nm in average particle size. Preferably, the average particle size of the nanodiamonds ranges from 10, 20, 30, 40, to 50 nm and more preferably about 20 to 40 nm.

The composite material may contain <0.1, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 20 or >2 wt. % of the nanodiamonds based on the total weight of the composite material. In some preferred embodiments, the composite material will contain about 0.5 to about 1.5 wt. % nanodiamonds.

In some embodiments, the nanodiamonds may be surface functionalized, for example, by arylation of oxidized or carboxylated nanodiamonds using phenylphosponate. In one example, for ND functionalization, ND particles were heat treated at 450° C. for 2 hours in air to produce functional groups on their surfaces; see Avazkonandeh-Gharavol M H, Sajjadi S A, Zebarjad S M, et al: *Effect of heat treatment of nanodiamonds on the scratch behavior of polyacrylic/nanodiamond nanocomposite clear coats*. Prog Organic Coatings 2013; 76:1258-1264 (incorporated by reference). A noticeable color change was found with high percent of ND (1.5%) while less or no color change was noticed with 0.5% ND.

In some embodiments, the method will involve further incorporation of one or more antimicrobial agents into the composite material along with nanodiamonds. These include plant oils and biological materials (e.g., rosemary oil, copaiba oil, propolis, shiitake powder, chitosan), quaternized ammonium monomers, metal or metal oxide nanoparticles including silver nanoparticles or titanium oxide nanoparticles, hydroxyapatite, nanoclay, carbon nanotubes or graphenes, silsesquioxane particles, and antibiotics or antifungal drugs. In other embodiments, the material comprises, consists essentially of, or consists of, PMMA and nanodiamonds without additional antimicrobial or antifungal agents or additional nanoparticles.

In one embodiment the composite material contains at least one natural oil selected from the group consisting of rosemary oil, copaiba oil, pepper mint oil, tea tree oil, sage oil, myrrh oil, clove oil, and eucalyptus oil in an amount of 0.05-10 wt %, preferably 0.1-5 wt %, 0.25-3 wt %, 0.5-2 wt %, 0.75-1.5 wt %, or 1.0-1.25 wt %, based on the total weight of the composite material.

The method as disclosed herein may use a composite material containing nanodiamonds which reduces the numbers of adherent *Candida albicans* to no more than <100, 95, 90, 80, 70, 60, 50, 40, 30, 20, or 10% of those attaching to an otherwise identical composite material not containing nanodiamonds.

Another embodiment of the invention is directed to a composite material suitable for use in dentures or dental implants comprising, consisting essentially of, or consisting of PMMA and nanodiamonds and, in some instances, any inevitable impurities produced during polymerization, mixing or other formulation steps for producing the composite material. In some embodiments, the PMMA is heat-cured, self-cured, radiation-cured, illumination-cured, or otherwise rendered solid by any other method. In other embodiments, the composite material may comprise other materials having sufficiently low porosity so as to be hygienic for extended placement in a wearer's mouth. These include plastics and other polymers such as acrylics or methacrylics.

In some embodiments, the composite material will contain nanodiamonds having an average particle size ranging from about 5 to 100 nm, preferably ranging from about 20, 25, 30, 35, or 40 nm in particle size.

In some embodiments, the composite material comprises nanodiamonds having an average diameter ranging from <10, 10, 20, 30, 40, 50, 60, 70, 80, 90, 100 or >100 nm in average particle size. Preferably, the average particle size of the nanodiamonds ranges from 10, 20, 30, 40, to 50 nm and more preferably about 20 to 40 nm. However, a nanodiamond particle size may be selected which provides a smooth surface to the produced composite material, for example, by filling and thus smoothing pores in the composite material. Preferably, the composite material containing nanodiamonds has a surface roughness $R_a$ of no more than 0.05, 0.06, 0.07, 0.08, 0.09, 0.1, 0.11, 0.12, 0.13, 0.14, 0.15, 0.16, 0.17, 0.18, 0.19, or 0.2 μm. Typically, the composite material containing nanodiamonds as disclosed herein will have a surface roughness less than that an otherwise similar composite material not containing the nanodiamonds or which contains equivalent amounts (wt. %) of metal or metal oxide nanoparticles, ceramic or glass nanoparticles, or carbon nanotubes.

Preferably, the nanodiamonds will be uniformly distributed within the composite material or uniformly distributed on the surface of the composite material. For example, in some embodiments, the wt % amount of the ND component between different unit volumes (e.g., mm³ or cm³) of the composite will not vary by more than 1, 2, 5, 10, 15, 20 or 25% or any intermediate value within this range.

Figure 4:
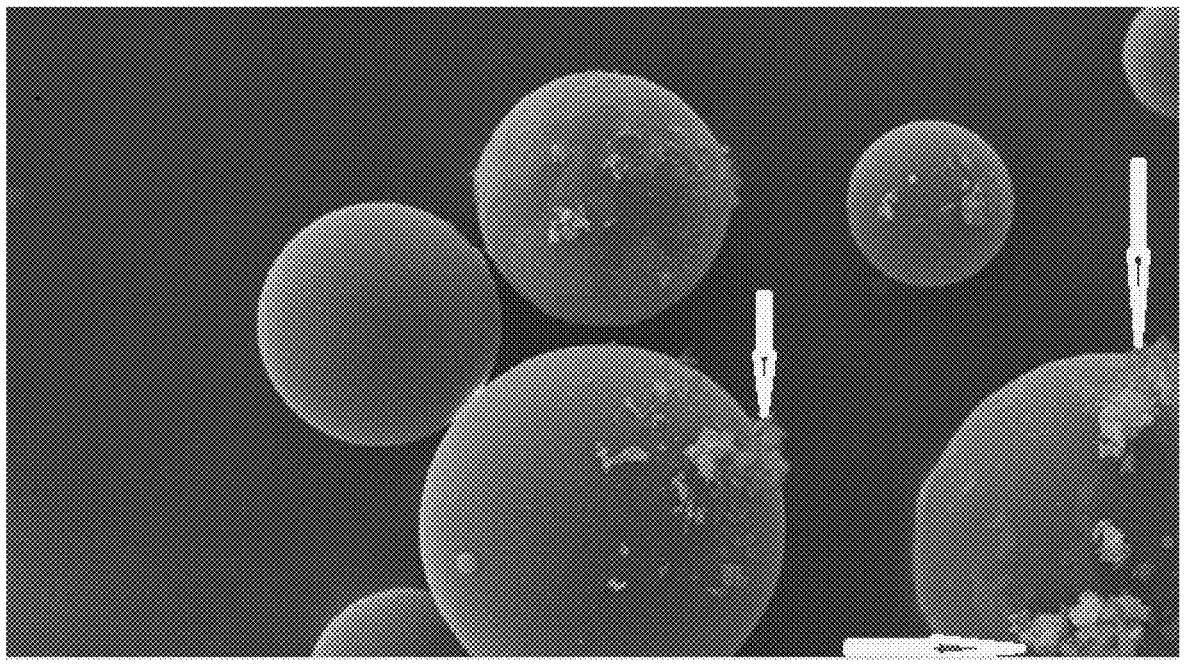
FIG. 4 shows a micrograph of ND-PMMA mixture.

In some embodiments the ND component will have a polydispersity index (Mw/Mn) ranging from 0.5, 0.6, 0.7, 0.75, 0.8, 0.85, 0.9, 0.95, <1 or 1 wherein 1 represents monodisperse ND particles. Distribution of ND mixed with acrylic powder can be analyzed using SEM. A polydispersity range of ND particles/sheets can be estimated from TEM images, wherein the diameter of nearly spherical sheets was determined to be as large as 150 nm and as small as 10 nm, e.g., ranging from about 10, 20, 30, 40, 50, 60, 70, 80, 90, 100, 110, 120, 130, 140, to about 150 nm. In one example, to ensure a homogenous and equal distribution of the filler, a ND/PMMA mixture was first stirred by glass mortar and pestle and then with an electric mixer for an appropriate time. The distribution of the ND NPs/sheets within the PMMA matrix was confirmed by SEM examination where ND sheets were thoroughly distributed and some PMMA spheres were coated with ND (see FIG. 4, orange arrows).

The composite material incorporating nanodiamonds as disclosed herein is typically used to produce dentures or other dental prosthetics, but in some embodiments, may be used in other devices, such as implants or bone grafts, or in insertable medical devices which may come into contact with yeasts or which require a smoother surface compared to devices made of a composite material like PMMA not containing the nanodiamonds.

Another embodiment is directed to a partial denture, full denture, orthopedic retainer, oral appliance, or other removable dental prosthetic comprising the composite material as disclosed herein which contains nanodiamonds. Other dental materials including implant material, a prosthetic material, a denture material, a filler, a denture plate material, a mold repairing material, or an impression material may incorporate the composite PMMA-ND of the invention.

Another embodiment of the invention is a method for making a denture or dental prosthetic comprising mixing a powder comprising nanodiamonds having a particle size of about 20 to 40 nm with methacrylic resin powder in a proportion of 98-99.75 wt. % of the resin powder to 2 to 0.25 wt. % nanodiamonds, heat polymerizing the mixture into PMMA, casting a denture base from the polymerized PMMA, and, polishing the denture base. In some embodiments, the polishing is continued until a desired surface roughness is attained, for example, a Ra of 0.2 μm or less. No difficulty was encountered during polishing PMMA-ND specimens which the inventors believe was due to the low percentages of NDs.

PMMA may be produced from methyl methacrylate by emulsion polymerization, solution polymerization, or bulk polymerization. Radical initiation may be used, but anionic polymerization of PMMA can also be performed. PMMA produced by radical polymerization is atactic and completely amorphous. All common molding processes may be used, including injection molding, compression molding, and extrusion to produce a denture base or other device. High quality PMMA sheets may be produced by cell casting where polymerization and molding steps occur concurrently. The strength of the material is higher than molding grades owing to its extremely high molecular mass. Rubber toughening or incorporation of rubber nanoparticles may be used to increase the toughness of PMMA and prevent brittleness in response to applied loads.

In some embodiments of the invention a different resin or acrylic resin other than PMMA may be used instead of or in admixture with PMMA. These include acrylic resin, modified acrylic resins, and composite resins and other suitable materials for dentures into which nanodiamonds may be incorporated. PMMA substitutes include materials used in different fields of medicine and dentistry, including for guided tissue regeneration, polymer reinforcement, and antibacterial dental implant coatings, as well as reinforcement of provisional resin of fixed prosthesis and gutta percha used for root canal treatment.

The cured denture part may be polished with pumice and/or a lathe, see for example Kuhar et al., *The effect of polishing technique on the surface roughness of acrylic denture base resin*. JPD. 2005; 93: 76-85 incorporated herein by reference, to obtain a Ra of 0.2 μm or less.

EXAMPLE

Materials and methods. Specimens were fabricated at the Prosthodontics Laboratory and tested at the Research Laboratory, College of Dentistry. Microbiology assays were carried out at the Department of Microbiology, College of Medicine, and SEM at the Electron Microscopy Unit, Institute for Research and Medical Consultations, Imam Abdulrahman Bin Faisal University.

ND/PMMA composite preparation. The nanodiamond (ND) powder (Shanghai Richem International Co. Ltd) had an average particle size of 30 nm. Transmission electron microscopy (TEM) was used to assess the surface morphological features of the powder, which showed that the powder consisted of graphite sheets (56% wt.) varying from a few to several tens of nanometers and NDs (44% wt.) with an estimated particle size by TEM of about 30 nm. NDs were added without further purification. Surface morphological features and composition were determined by transmission electron microscopy (TEM) which showed that the ND powder consisted of graphite sheets (56 wt %) varying from a few to several tens of nanometers and NDs (44 wt %) had an approximate particle size of 30 nm.

The NDs were weighed with an electronic balance (S-234, Denver instrument) in concentrations of 0.5, 1, and 1.5 wt. % of the acrylic resin powder. The mix was stirred first with gentle hand pressure using a conventional mortar and pestle, then with an electric mixer for half an hour at 400 rpm to ensure equal dispersion of the filler in the resin powder; see Al-Harbi, et al., J Prosthodont. 2019; 28:417-425, incorporated by reference.

Figure 3:
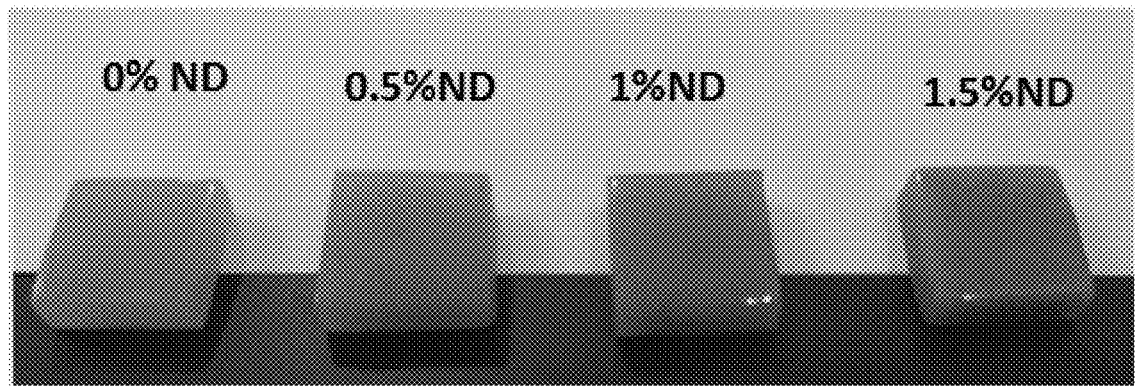
FIG. 3 shows PMMA-ND specimens containing 0, 0.5, 1.0 and 1.5 wt % nanodiamonds.

Specimen fabrication. Heat-polymerized acrylic was used to fabricate 120 specimens resin (Table 1, Major base 20 resin; Prodotti Dentari SPA). The specimens were divided into four groups according to their ND concentrations, each including 30 specimens. Metal molds were used to fabricate wax specimens 10×10×3 mm$^3$ in size, then the wax specimens were invested in dental stone (Fujirock E P; G C) within flasks (61B Two Flask Compress; Handler Manufacturing). After the setting of the stone was complete, the flasks were placed into a wax elimination machine for five minutes to dissolve the wax. Some examples of PMMA-ND composites are shown in FIG. 3. The PMMA-ND composite is typically used for a denture base which contacts a person's gums.

The resulting mold spaces and all the stone surfaces were coated with a separating medium (Isolmajor; Major Prodotti Dentari Spa). A porcelain jar was used for mixing the polymer and monomer according to the manufacturer's guidelines.

When the mix reached the dough stage, it was hand-kneaded, then packed and processed in a heat-curing unit (KaVo Elektrotechnisches Werk GmbH, Leutkirch, Germany) for two hours at 74° C., followed by one hour at 100° C.

Before deflasking, the flasks were left to cool to room temperature.

The specimens were finished and polished with a tungsten carbide bur (HM 79GX-040 HP; Meisinger) with a thin cross cut at 18,000 rpm, followed by a fine-grain cylindrical rubber top bur for the acrylic resin (HM251FX-040-HP; Meisinger); Al-Harbi F A, et al. *Effect of nanodiamond addition on flexural strength, impact strength, and surface roughness of PMMA denture base*. J Prosthodont. 2019; 28:417-425 (incorporated by reference).

To standardize the polishing procedures, definitive polishing on a polishing cloth disc (TexMet C10in, 42-3210, Buehler GmbH) was carried out with a mechanical polisher (Metaserve 250 grinder-polisher, Buehler) at 100 rpm for five minutes in wet conditions; Al Habi, et al., id. After ultrasonic cleaning, the specimens were incubated for one week at 37° C. in distilled water that was changed daily to reduce the accumulation of residual monomers; Murat S, et al. *In Vitro Evaluation of Adhesion of Candida albicans on CAD/CAM PMMA-Based Polymers*. J Prosthodont. 2019 February; 28(2):e873-e879.

Polishing was done in conventional technique followed for denture base polishing and to standardize the polishing technique we used a mechanical polisher as follow: definitive polishing on a polishing cloth disc (TexMet C10in, 42-3210, Buehler GmbH) was carried out with a mechanical polisher (Metaserve 250 grinder/polisher, Buehler) at 100 rpm for five minutes in wet conditions.

TABLE 1

Composition of heat cured acrylic resin and artificial saliva.

| Materials | Name and manufacturer | Composition |
|---|---|---|
| Artificial Saliva | A. S. Orthana, Biofac A/S, Kastrup, Denmark | Mucin, methyl-4-hydroxybenzoate, benzalconium chloride, ethylenediaminetetraacetic acid (EDTA), H2O2, xylitol, peppermint oil, spearmint oil and mineral salts |
| Major.Base.20 Resin | Prodotti Dentari SPA, Moncalieri, Italy; Powder lot no. 14030P; Liquid lot no. 1402VP | Powder: Methyl methacrylate (MMA), polymers, benzoyl peroxide; Form: Micropearls; Liquid: MMA, ethylene glycol, dimethacrylate, N,N-dimethyle-p-toluidine, benzophenone-3 |

Surface roughness test. A non-contact optical interferometric profilometer (Contour Gt-K1 optical profiler; Bruker Nano, Inc., Tucson, Ariz.) was used to measure the Ra (surface roughness) of the specimens at a 0.01 mm resolution. The specimens (approximate area 0.43×0.58 mm) were scanned with a standard camera at 20× at five sites, and the average for each specimen was calculated. A software package (Vision64, Bruker Nano) was used to analyze the acquired images. Pit characteristics were determined, and the Ra value of each specimen was calculated.

Scanning electron microscopy (SEM). The scanning electron microscope (SEM) (FEI, ISPECT S50) was used to examine the specimens' surface characteristics (topography). To avoid the non-conductive property of the material, a gold coating was applied with a sputter coating machine (Quorum, Q150R ES, UK). Images were captured at different magnifications (500, 1000, 2000, 5000, and 10 000×) to observe important characteristics of the surface changes with different ND concentrations.

Contact angle measurement. After the surface roughness test, the surfaces of the specimens were gently dried with air. Droplets of distilled water were then applied on the surface of the specimens using an auto pipette and a goniometer to standardize the droplets volume (2 µL). An automated contact angle goniometer (DM-501; Kyowa Interface Science Co, Japan) was used to measure the contact angle. The angle of the tangent to the surface of the water droplet was measured and repeated four times on different areas of each specimen. Thereafter, the average was calculated. The images were analyzed with FAMAS software (Kyowa Interface Science Co, Japan).

Microbiology test. The specimens were sterilized with 70% alcohol, then cleaned ultrasonically with sterilized distilled water; Mura, et al. (2019), id. The sterilized specimens were soaked in artificial saliva (Table 1) containing 2,000,000 cells of *Candida albicans* (ATCC 10231) at 37° C. for 48 hours; Ali, A A, et al. (2013), id., Nawasrah, A, et al. 02016), id., Gad M M, et al., *Inhibitory effect of zirconium oxide nanoparticles on Candida albicans adhesion to repaired polymethyl methacrylate denture bases and interim removable prostheses: a new approach for denture stomatitis prevention.* Int J Nanomedicine. 2017; 12:5409.

To detach non-adherent cells, phosphate-buffered saline (PBS) was used to wash the acrylic plates three times. The plates were then put into sterile tubes containing 1 ml of Sabouraud's dextrose broth (SDB-Acumedica Co., Manufacturers, Inc.) for 24 hours. After that, the plates were vibrated for 10 minutes with a vortex mixer. To obtain clustered pellets of *Candida albicans*, the tubes were then centrifuged for five minutes at 4,500 rpm.

After being centrifuged, the acrylic resin specimens were extracted from the tubes, and the clustered pellets were collected from the tube. The *Candida albicans* attached to each specimen was counted by two methods:

Slide count method (Neubauer): For microscopic evaluation, 2.5 µl of Trypan Blue 0.4% solution in phosphate (MP-Biomedicals) was added to 7.5 µl of each concentrated *Candida* pellet of the specimen positioned on a slide worktable (Neubauer Slide Counter; Chambers-Marienfeld). The Trypan Blue stain distinguishes the living *Candida albicans* from the dead by showing the living *Candida albicans* cells as transparent and surrounded by a blue borderline, while the dead cells were colored blue. A light microscope (at low power magnifications,10×) was used to count the number of *Candida albicans* cells. Each slide contained four main squares, each of which was divided into 16 smaller squares. *Candida albicans* cells were counted in two main squares, then multiplied by two to achieve the total number of *Candida albicans* on each slide; Ali, A A, et al. (2013), id; Nawasrah, A, et al. (2016), id.

Direct culture method: [colony-forming unit (CFU)] 10 µl of each isolated centrifuged pellet was spread onto a petri dish and incubated for 24 hours at 37° C.; Gad, M M. et al., (2017), id. A marker pen counter (colony counter "SP Scienceware, Bel-Art Products") was used to count the *Candida albicans* colonies. The number of colonies was calibrated for the dilution factor. When the number of colonies reached 5,000 or more, it was considered overgrown.

Statistical analysis. An IBM SPSS Statistics 23 (IBM Corp., Armonk, N.Y.) was used for all statistical analyses. Arithmetic means and standard deviations for categorized parameters were calculated. ANOVA was used to check overall significance, and pairwise significance was tested by using Tukey' s post hoc test. The level of significance was set at $P<0.05$.

In comparison to the control group, the addition of NDs significantly reduced the surface roughness ($P<0.05$) (Table 2). The highest Ra value was found with the control group (0.129±0.011 µm), while the lowest value was with 0.5% NDs group (0.039±0.009 µm) with no significant difference between 0.5% NDs and 1% NDs groups ($P=0.396$).

Significant differences were seen between the 0.5% NDs and 1% NDs groups and the 1.5% NDs group ($P<0.05$), which showed the highest Ra value of the NDs groups.

FIG. 1 shows the color parameter that represents the average Ra values ranging from red at the parameter top to blue at the parameter bottom. Where rough surfaces have peaks, valleys, and areas in between, red reveal the peaks while blue reveals the valley depth, and the interdigitated colors in between exhibited areas between the peaks and valleys. Thus, the graduated color of this parameter displayed the whole surface roughness. FIGS. 1A, 1B, 1C and 1D, respectively, depict surface roughness for (unmodified specimens, 0.5% nanodiamond (ND) concentration; 1% ND concentration; and 1.5% ND concentration.

FIG. 2 shows SEM micrographs of the surface of the specimens at 5000× magnification with different concentrations of NDs. SEM analysis displayed high Ra in unreinforced heat-cured acrylic resin (FIG. 2A) containing broad scattered pores with dimensions of 80 to 100 microns and depth variations.

FIG. 2B (0.5% NDs) shows a compact morphology with diminutive pores preoccupied by NDs measuring a few microns in diameter.

FIG. 2C (1% NDs) and FIG. 2D (1.5% NDs) show smooth surfaces resulting from NDs filling the pores. FIG. 2D also shows loosely attached clusters of NDs on the surface of the specimens.

The mean and standard deviations to surface roughness in these samples is described by Table 2.

TABLE 2

Mean and standard deviations of surface roughness of studied group

| Group | Control | 0.5% ND | 1% ND | 1.5% ND |
|---|---|---|---|---|
| Mean ± SD | $0.129 \pm 0.011$ | $0.039 \pm 0.009^A$ | $0.047 \pm 0.007^A$ | $0.102 \pm 0.017$ |
| | F-value (149.089) | | P-value (0.000) | |

Table 3 shows the mean values of the contact angles in each group against distilled water. No significant difference was found in contact angles between all the tested groups ($p=0.083$) or between the control group and the NDs-reinforced groups ($p>0.05$). The highest contact angle value was $84.8\pm1.62$, recorded with the 1.5% NDs group, while the lowest contact angle value was $82.4\pm1.8$, recorded with the 0.5% NDs group.

TABLE 3

Mean and standard deviations of contact angles in all tested groups

| Group | Control | 0.5% ND | 1% ND | 1.5% ND |
|---|---|---|---|---|
| Mean ± SD | $82.9 \pm 3.14^A$ | $82.4 \pm 1.8^A$ | $83\pm1.63^A$ | $84.8 \pm 1.62^A$ |
| | F-value = 11.025 | | P-value = 0.083 | |

Table 4 shows the means and standard deviations of all the tested groups regarding the Neubauer and CFU tests.

Regarding Neubauer, the *Candida albicans* count in the control group showed a significant increase compared with the other NDs groups (P<0.05), the lowest *Candida albicans* count occurring in the 1% NDs group (276.2±34.47). In the NDs groups, the 0.5% NDs group showed a significant difference compared with the 1% and 1.5% NDs groups, while the 1% NDs and 1.5% NDs groups showed no significant difference between them.

The number of living *Candida albicans* cells was obtained with a culture test.

The CFU method revealed a significant increase in the *Candida albicans* count in the control group compared to the NDs groups (P<0.05), with the lowest CFU count occurring in the 1% NDs group (2848.6±187.8). In the NDs groups, the 0.5% NDs group showed a significant difference compared with the 1% and 1.5% NDs groups, while the 1% and 1.5% NDs groups showed no significant difference between them. The number of *Candida albicans* observed with the CFU test decreased significantly with the addition of NDs, especially in the 1% and 1.5% NDs groups.

The Neubauer and CFU test methods showed no statistically significant difference, which confirmed the effect of NDs against *Candida albicans*, as their effect was approximately the same regardless of concentration.

TABLE 4

Mean and standard deviations of different studied groups regarding slide count (Neubauer) and colony forming unit (CFU).

| Group | Neubauer | CFU |
|---|---|---|
| Control | $2035.9 \pm 121.03^a$ | $13212.0 \pm 821.2^A$ |
| 0.5 ND | $1039.4 \pm 88.11^b$ | $7604.7 \pm 310.97^B$ |
| 1 ND | $276.2 \pm 34.47^c$ | $2848.6 \pm 187.8^C$ |
| 1.5 ND | $303.3 \pm 35.93^{cd}$ | $3602.0 \pm 339.25^{CD}$ |
| F | 21.36 | 104.2 |
| P | 0.01* | 0.0001* |

Lower case letters a, b, c and d indicate slide count tests. Upper case letters A, B, C and D indicate cell culture counts. In Tables 2-4: F=ANOVA test, One-way ANOVA and Tukey's post hoc test (p<0.05) indicate differences among NDs concentrations. Differences are indicated by superscripts which are lettered vertically where use of the same letter, e.g., "cd" or "CD" indicates no significant difference.

The results revealed a significant decrease in *Candida albicans* adhesion with the addition of NDs in comparison with the control group.

Surprisingly, incorporation of nanodiamonds into the PMMA dental base significantly reduced surface roughness compared to the control group but the water contact angles were not significantly changed. The first research hypothesis was partly rejected because the surface roughness of the NDs-PMMA groups was significantly reduced compared to the control group, while the contact angle values showed no significant change. This result suggests that incorporation of nanodiamonds into PMMA would reduce the ability of *Candida albicans* to attach to the composite dental composite material because *Candida albicans* attaches better to rough surfaces with greater surface area for colonization.

The present study showed a significant decrease in the *Candida albicans* count in the NDs groups compared with the control group, which had the highest Ra value. According to the surface roughness test and SEM analysis, the addition of NDs to PMMA improved the surface structure of the specimens, which could contribute to the prevention of *Candida albicans* adhesion.

In comparison with the control group, SEM analysis showed that the addition of NDs changed the surface profile of the tested specimens by filling the pores. After complete saturation, NDs formed clusters on the surface of the specimens.

While not being bound to any particular theory, the inventors believe that reduced surface roughness may have resulted from the nanodiamond particles' small size, which reduced the inter-particle distance, resulting in close contacts between the nanoparticles at lower concentrations. While an increase in Ra was observed with a high concentration of NDs (1.5%), even at this higher concentration of NDs, the surface roughness was still lower than in the control group and within a clinically acceptable value of about 0.2 μm; see Radford D R, et al., *Adherence of Candida albicans to denture base materials with different surface finishes*. J Dent. 1998 Sep. 1;26(7):577-83. This increase in the sample containing 1.5 wt. % ND, may have resulted from spaces created on the surface of the specimens due to the separation of loosely attached clusters of NDs particles after finishing and polishing. The reduced Ra of PMMA incorporating NDs may have resulted from improved polishability due to the presence of small nanofillers merging within the denture base resin, providing a smooth polished surface.

The addition of NDs to PMMA showed no significant change in the contact angles of the specimens containing NDs in comparison to the control group. This result is surprising because disagrees with those of several studies that reported changes in the PMMA contact angle with the addition of nanofillers. Increasing carbon nanotube content of PMMA in the 1-2 wt % range increased the water contact angle; Kim K I, et al., *Carbon nanotube incorporation in PMMA to prevent microbial adhesion*. Scientific reports. 2019 Mar. 20; 9(1):4921. Such an increase would enhance adhesion of *Candida albicans*; Sipahi C, et al. *The effect of acquired salivary pellicle on the surface free energy and wettability of different denture base materials*. J Dent 2001; 29:197-204.

The Neubauer and CFU tests showed a significant decrease in the *Candida albicans* count in the NDs groups compared with the control group. The lowest *Candida albicans* count in both tests occurred in the 1% NDs group.

The effect of NDs against *Candida albicans* adhesion has not previously been disclosed *Candida albicans* is the main causative pathogen of denture stomatitis, which affects many complete denture subjects. As disclosed herein, the addition of nanodiamonds (NDs) to polymethylmethacrylate (PMMA) denture composite material significantly decreased surface roughness and *Candida albicans* adhesion to the composite material with the lowest values observed at 1% NDs and 0.5% NDs, respectively, while not significantly affecting contact angle (i.e. not increasing hydrophobicity). These properties are advantageous in treating dental diseases such as dental stomatitis caused by *Candida*. These results show that PMMA/NDs composites are valuable for prevention of denture stomatitis which is considered one of the most common clinical problems among removable denture wearers.

Terminology. Terminology used herein is for the purpose of describing particular embodiments only and is not intended to be limiting of the invention.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:
1. A method for reducing the severity of denture stomatitis comprising:
  providing a subject who has denture stomatitis with a
    replacement denture comprising a denture base made of a composite material that contains a polymer suitable for use as a denture base into which nanodiamonds have been incorporated, wherein the polymer comprises poly(methylmethacrylate) (PMMA) with a molecular weight of 50,000 to 1,000,000 g/mol, wherein the composite material is porous having pores 80 to 100 μm in size, wherein the nanodiamonds fill pores of the composite material, where the nanodiamonds are only in the pores on the composite material, wherein the composite material comprises 0.1 to 1.0 wt. % nanodiamonds, relative to a total weight of the composite material, wherein the composite material has a surface roughness ($R_a$) of no more than 0.2 μm.

2. The method of claim 1, wherein the subject has cancer, is immunosuppressed, is being treated with an antimicrobial drug, has high blood sugar or diabetes, or is otherwise at risk of developing an infection by Candida.

3. The method of claim 1, wherein the denture stomatitis is caused by a member of the genus *Candida*.

4. The method of claim 1, wherein the denture stomatitis is caused by *Candida albicans*.

5. The method of claim 1, wherein the polymer comprises PMMA and rubber nanoparticles.

6. The method of claim 1, wherein the nanodiamonds have an average particle size ranging from 20-40 nm.

7. The method of claim 1, wherein the nanodiamonds have an average particle size of about 30 nm and/or the nanodiamonds are uniformly distributed in the composite material so that the density of nanodiamonds between $cm^3$ different volumes of composite does not vary by more than 10%.

8. The method of claim 1, wherein the composite material comprises 0.1 to 0.5 wt. % nanodiamonds, relative to a total weight of the composite material.

9. The method of claim 1, wherein the PMMA has a molecular weight of 200,000 to 500,000 g/mol.

10. The method of claim 1, wherein the composite material has an $R_a$ of no more than 0.15 μm.

11. The method of claim 1, wherein the composite material has an $R_a$ of no more than 0.1 μm.

* * * * *